US005913823A

United States Patent [19]
Hedberg et al.

[11] Patent Number: 5,913,823
[45] Date of Patent: Jun. 22, 1999

[54] ULTRASOUND IMAGING METHOD AND SYSTEM FOR TRANSMIT SIGNAL GENERATION FOR AN ULTRASONIC IMAGING SYSTEM CAPABLE OF HARMONIC IMAGING

[75] Inventors: David J. Hedberg; Stuart L. Carp, both of Menlo Park; Stirling S. Dodd, San Jose; Samual H. Maslak, Woodside; Bhaskar S. Ramamurthy, San Jose; Daniel E. Need, Mountain View; John A. Hossack, Palo Alto, all of Calif.

[73] Assignee: Acuson Corporation, Mountain View, Calif.

[21] Appl. No.: 08/893,150

[22] Filed: Jul. 15, 1997

[51] Int. Cl.⁶ .......................................................... A61B 8/00
[52] U.S. Cl. ............................................. 600/443; 600/458
[58] Field of Search ........................... 600/437, 440–443, 600/447, 458

[56] References Cited

U.S. PATENT DOCUMENTS

| | | |
|---|---|---|
| 4,688,430 | 8/1987 | Anderson .................................... 73/625 |
| 4,712,037 | 12/1987 | Verbeek et al. . |
| 5,040,537 | 8/1991 | Katakura . |
| 5,111,823 | 5/1992 | Cohen . |
| 5,115,809 | 5/1992 | Saitoh et al. . |
| 5,190,766 | 3/1993 | Ishihara . |
| 5,195,520 | 3/1993 | Schlief et al. . |
| 5,215,680 | 6/1993 | D'Arrigo . |
| 5,219,401 | 6/1993 | Cathignol et al. . |
| 5,255,683 | 10/1993 | Monaghan . |
| 5,269,189 | 12/1993 | Thompson et al. ........................ 73/632 |
| 5,358,466 | 10/1994 | Aida et al. . |
| 5,380,411 | 1/1995 | Schlief . |
| 5,410,205 | 4/1995 | Gururaja . |
| 5,410,516 | 4/1995 | Uhlendorf et al. . |
| 5,417,214 | 5/1995 | Roberts et al. . |

(List continued on next page.)

FOREIGN PATENT DOCUMENTS

| | | |
|---|---|---|
| 0 357 164 | of 0000 | European Pat. Off. . |
| 0 770 352 A1 | 5/1997 | European Pat. Off. . |
| WO 98/20361 | 5/1998 | WIPO . |

OTHER PUBLICATIONS

U.S. application No. 08/642,528, (Attorney Docket No. 5050/136), filed May 3, 1996.
U.S. application No. 08/661,227, (Attorney Docket No. 5050/70), filed Jun. 10, 1996.
U.S. application No. 08/771,345, (Attorney Docket No. 5050/164), filed Dec. 16, 1996.
U.S. application No. 08/838,919, (Attorney Docket No. 5050/198), filed Apr. 11, 1997.
Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1995.
Marc Gensane, "Bubble population measurements with a parametric array." J. Acoustical Society of America, 95 (6), Jun. 1994.
Ken Ishihara, et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

(List continued on next page.)

*Primary Examiner*—Francis J. Jaworski
*Attorney, Agent, or Firm*—Craig A. Summerfield, Esq.; Brinks Hofer Gilson & Lione

[57] ABSTRACT

An improvement to the method for harmonic imaging including the steps of (a) transmitting ultrasonic energy at a fundamental frequency and (b) receiving reflected ultrasonic energy at a harmonic of the fundamental frequency is provided. For the improvement, the transmitting step includes the step of transmitting a uni-polar waveform or a waveform characterized by an amplitude change rate of 8 or fewer times pre carrier cycle, said waveform comprising an envelope shape rising gradually to a respective maximum value and falling gradually from the respective maximum value.

51 Claims, 12 Drawing Sheets

U.S. PATENT DOCUMENTS

| | | |
|---|---|---|
| 5,425,366 | 6/1995 | Reinhardt et al. . |
| 5,433,207 | 7/1995 | Pretlow, III . |
| 5,438,554 | 8/1995 | Seyed-Bolorforosh et al. . |
| 5,456,255 | 10/1995 | Abe et al. . |
| 5,456,257 | 10/1995 | Johnson et al. . |
| 5,469,849 | 11/1995 | Sasaki et al. . |
| 5,479,926 | 1/1996 | Ustuner et al. . |
| 5,482,046 | 1/1996 | Deitrich . |
| 5,523,058 | 6/1996 | Umemura et al. ............... 422/128 |
| 5,526,816 | 6/1996 | Arditi . |
| 5,558,092 | 9/1996 | Unger et al. . |
| 5,560,364 | 10/1996 | Porter . |
| 5,577,505 | 11/1996 | Brock-Fisher et al. . |
| 5,579,768 | 12/1996 | Klesenski . |
| 5,579,770 | 12/1996 | Finger . |
| 5,580,575 | 12/1996 | Unger et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,632,277 | 5/1997 | Chapman et al. . |
| 5,675,554 | 10/1997 | Cole et al. . |
| 5,678,554 | 10/1997 | Hossack et al. . |
| 5,724,976 | 3/1998 | Mine et al. ...................... 600/459 |

OTHER PUBLICATIONS

V.L. Newhouse, et al., "Bubble size measurements using the nonlinear mixing of two frequencies." J. Acoustical Society of America, 75 (5), May 1984.

"Small Spheres Lead to Big Ideas." Research News, Science vol. 267, Jan. 20, 1995.

Abstracts Journal of the American Society of Echocardiography, vol. 8, No. 3, pp. 345–346, 355, 358–364.

Deborah J. Rubens, MD, et al., "Sonoelasticity Imaging of Prostate Cancer: In Vitro Results." Radiology, vol. 195, No. 2, 1995.

B. Schrope, et al., "Simulated Capillary Blood Flow Measurement Using a Nonlinear Ultrasonic Contrast Agent." Ultrasonic Imaging 14 (1992).

Fred Lee, Jr., MD, et al., "Sonoelasticity Imaging: Results in in Vitro Tissue Specimens." Radiology, vol. 181, No. 1 (1991).

Kevin J. Parker, PhD., et al., "Sonoelasticity of Organs: Shear Waves Ring A Bell." J. Ultrasound Med., 11 (1992).

William Armstrong, M. D., et al., "Position Paper on Contrast Echocardiography." American Society of Echocardiography, draft 1, Jun. 6, 1994.

K.J. Parker, et al., "Tissue Response to Mechanical Vibrations for 'Sonoelasticity Imaging'." Ultrasound in Med. and Biol., vol. 16, No. 3, (1990).

Robert M. Lerner, et al., "'Sonoelasticity 'Images Derived from Ultrasound Signals in Mechanically Vibrated Tissues." Ultrasound in Med. and Biol., vol. 16, No. 3 (1990).

excerpt from Ultrasonics: Fundamentals and Applications (1992), pp. 380–393, 363–365.

J.A. Hossack, et al., "Improving Transducer Performance Using Multiple Active Layers." SPIE vol. 1733 (1992).

Volkmar Uhlendorf, et al., "Nonlinear Acoustical Response of Coated Microbubbles in Diagnostic Ultrasound." IEEE 1994 Ultrasonics Symposium.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

H. Edward Karrer, et al., "A Phased Array Acoustic Imaging System for Medical Use." IEEE 1980 Ultrasonics Symposium.

"HP Ultrasound Technologies —Viability." About HP Ultrasound Imaging, WWW document, 1997.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

"Supplement to Journal of the American College of Cardiology." American College of Cardiology, 45$^{th}$ Annual Scientific Session, Mar. 24–27, 1996 pp. 21A, 63A, 239–240A.

Yang–Sub Lee, et al., "Time–Domain Modeling of Pulsed Finite–Amplitude Sound Beams." J. Acoustical Society of America, 97 (2), Feb. 1995.

Michalakis A. Averkiou, et al., "Self–Demodulation of Amplitude and Frequency–Modulated Pulses in a Thermoviscous Fluid." J. Acoustical Society of America, 94 (5), Nov. 1993.

Powers, J.E. "Ultrasonic Diagnostic Imaging with Contrast Agents," EP 0770352A1 Publ., May 2, 1997.

Takeuchi, "Coded Excitation For Harmonic Imaging," 1996 IEEE UTS Symposium pp. 1433–1436.

N CHANNELS 40 (TRANSMIT BEAMFORMER)

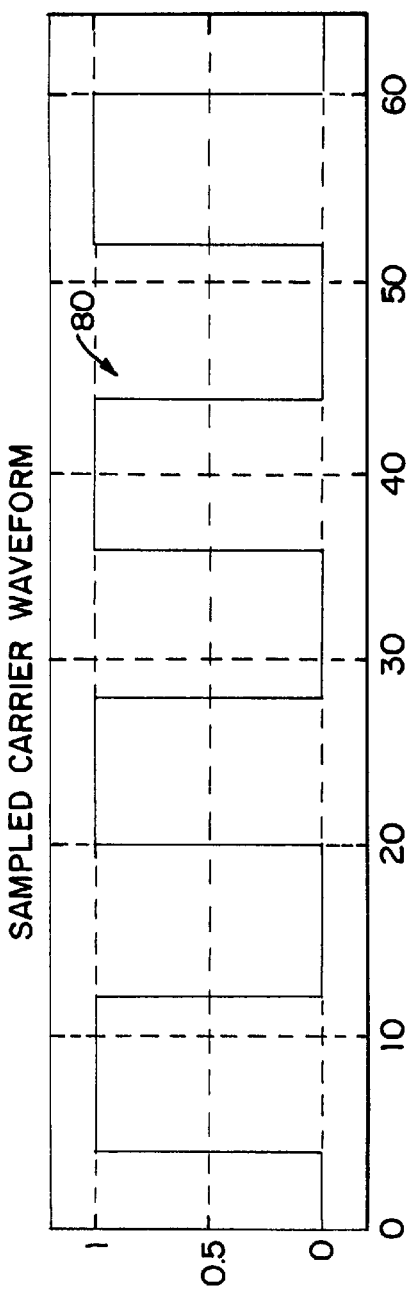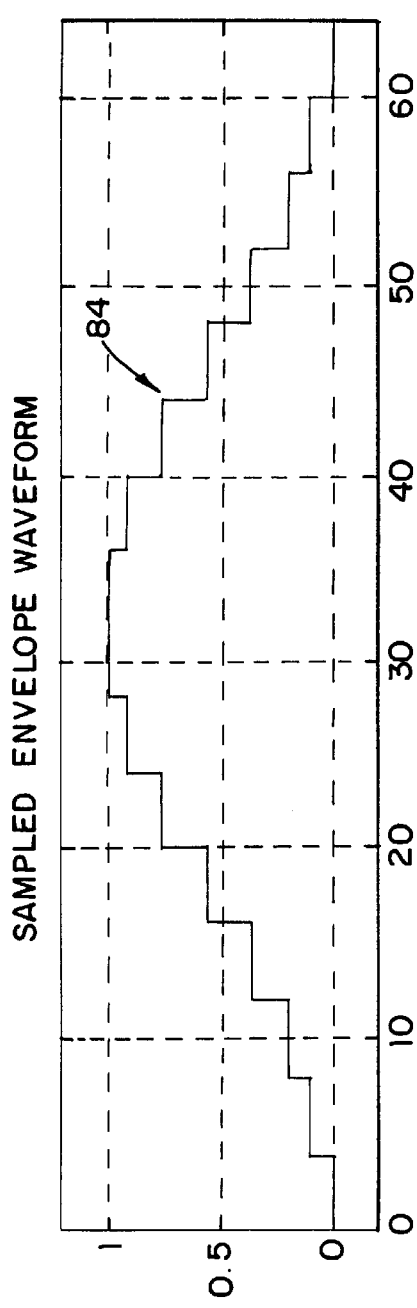

5,913,823

ULTRASOUND IMAGING METHOD AND SYSTEM FOR TRANSMIT SIGNAL GENERATION FOR AN ULTRASONIC IMAGING SYSTEM CAPABLE OF HARMONIC IMAGING

FIELD OF THE INVENTION

This invention generally relates to ultrasonic imaging systems. In particular, the invention relates to improved systems and methods for imaging using harmonic frequency signals.

BACKGROUND OF THE INVENTION

Ultrasound imaging systems generate and transmit ultrasound signals. The systems typically have several imaging modes, such as B-mode, color flow, and spectral Doppler.

The transmitted ultrasound signals have optimal characteristics set in response to the selected mode. The characteristics include frequency and bandwidth. As an example, B-mode imaging uses transmitted signals with a wide bandwidth and high frequency. As another example, color flow imaging uses transmitted signals with narrow bandwidth and lower frequency as compared to B-mode imaging.

Another type of imaging is harmonic imaging. Harmonic imaging is generally associated with imaging tissue or contrast agents at harmonic frequencies.

Typically, the transmitted ultrasound signal is a burst of sinusoidal waves associated with rectangular or sinusoidal transmit waveforms applied to the transducer. The transmitted signal has a center frequency within the 1 to 15 MHz range. The ultrasound signal propagates through a body. The ultrasound signal reflects off structures within the body, such as tissue boundaries. Some of the reflected signals, or echo signals, propagate back towards the transducer.

As the transmit signal propagates through and scatters within the body, additional frequency components are generated, such as at harmonics of the transmit frequency. These additional frequency components continue to propagate through and reflect off structures in the body. Echo signals having the same frequencies as the transmit signal and echo signals associated with the additional frequency components impinge on the transducer. The additional frequency components are caused by non-linear effects, such as non-linear propagation.

The harmonic signals may also be generated by ultrasound contrast agents. The contrast agents are typically gas or fluid filled micro-spheres which resonate at ultrasound frequencies. The contrast agents are injected in the blood stream and carried to various locations in the body. When insonified, harmonic echo signals are generated due to resonance within the contrast agents.

The echo signals are received, processed and detected by the ultrasound system. For harmonic imaging, energies associated with fundamental or transmit frequencies are removed by receive filtering. Thus, echo signals resulting from non-linear propagation and reflection are detected by the ultrasound system. However, the transmitted burst may include significant energy at the harmonic frequencies. The transmitted energy masks the non-linear response of the body and interferes with the harmonic signals from any contrast agents.

To improve harmonic imaging, it is known to reduce the energy at the harmonic in the transmit burst. The energy at the harmonic is reduced by generating a Gaussian envelope, complex sinusoidal waveform for each channel of a transducer. However, transmit beamformers capable of generating such a complex waveform require expensive components.

The present invention is directed to further improvements that enhance the imaging of the non-linear response of a body.

SUMMARY OF THE INVENTION

The invention relates to improvements to a method for harmonic imaging, method comprises the steps of (a) transmitting ultrasonic energy at a fundamental frequency and (b) receiving reflected ultrasonic energy at a harmonic of the fundamental frequency.

According to a first aspect of this invention, the transmitting step includes the step of transmitting a uni-polar waveform comprising an envelope shape rising gradually to a respective maximum value and falling gradually from the respective maximum value.

According to a second aspect of this invention, the transmitting step includes the step of transmitting a waveform characterized by an amplitude change rate of 8 times or fewer during a carrier signal cycle, said waveform comprising an envelope shape rising gradually to a respective maximum value and falling gradually from the respective maximum value.

According to a third aspect of this invention, the transmitting step includes the step of transmitting a waveform comprising an envelope shape rising gradually to a respective maximum value and falling gradually from the respective maximum value, wherein the waveform is responsive to a uni-polar signal and a shaped signal.

According to a fourth aspect of this invention, the transmitting step includes the step of generating a stepped pulse waveform comprising an envelope shape rising gradually to a respective maximum value and falling gradually from the respective maximum value.

According to a fifth aspect of this invention, the transmitting step includes the step of generating a waveform comprising a plurality of amplitudes selected from the group of: a plurality of positive amplitudes and a plurality of negative amplitudes, wherein the amplitudes each comprise a duration representing a step and wherein the envelope of said amplitudes rises gradually to a respective maximum value and falls gradually from the respective maximum value.

According to a sixth aspect of this invention, a method of generating a waveform transmitted from at least one of a plurality of transducer elements for harmonic imaging is provided. The method includes the steps of: generating a rectangular waveform carrier signal; modulating the rectangular wave carrier signal with an envelope signal comprising a gradually increasing and gradually decreasing amplitude; and transmitting a waveform responsive to data created by modulating.

According to a seventh aspect of this invention, a method of generating a uni-polar waveform transmitted from at least one of a plurality of transducer elements for harmonic imaging is provided. The method includes the steps of: generating a bi-polar waveform; off-setting the bi-polar waveform with an off-set signal comprising a gradually increasing and gradually decreasing envelope; and transmitting the uni-polar waveform responsive to data created by off-setting the bi-polar waveform.

BRIEF DESCRIPTION OF THE DRAWINGS

FIG. 3C is a graphical representation of a carrier waveform.

FIG. 3D is a graphical representation of an envelope waveform.

DETAILED DESCRIPTION OF PREFERRED EMBODIMENTS

Figure 1:
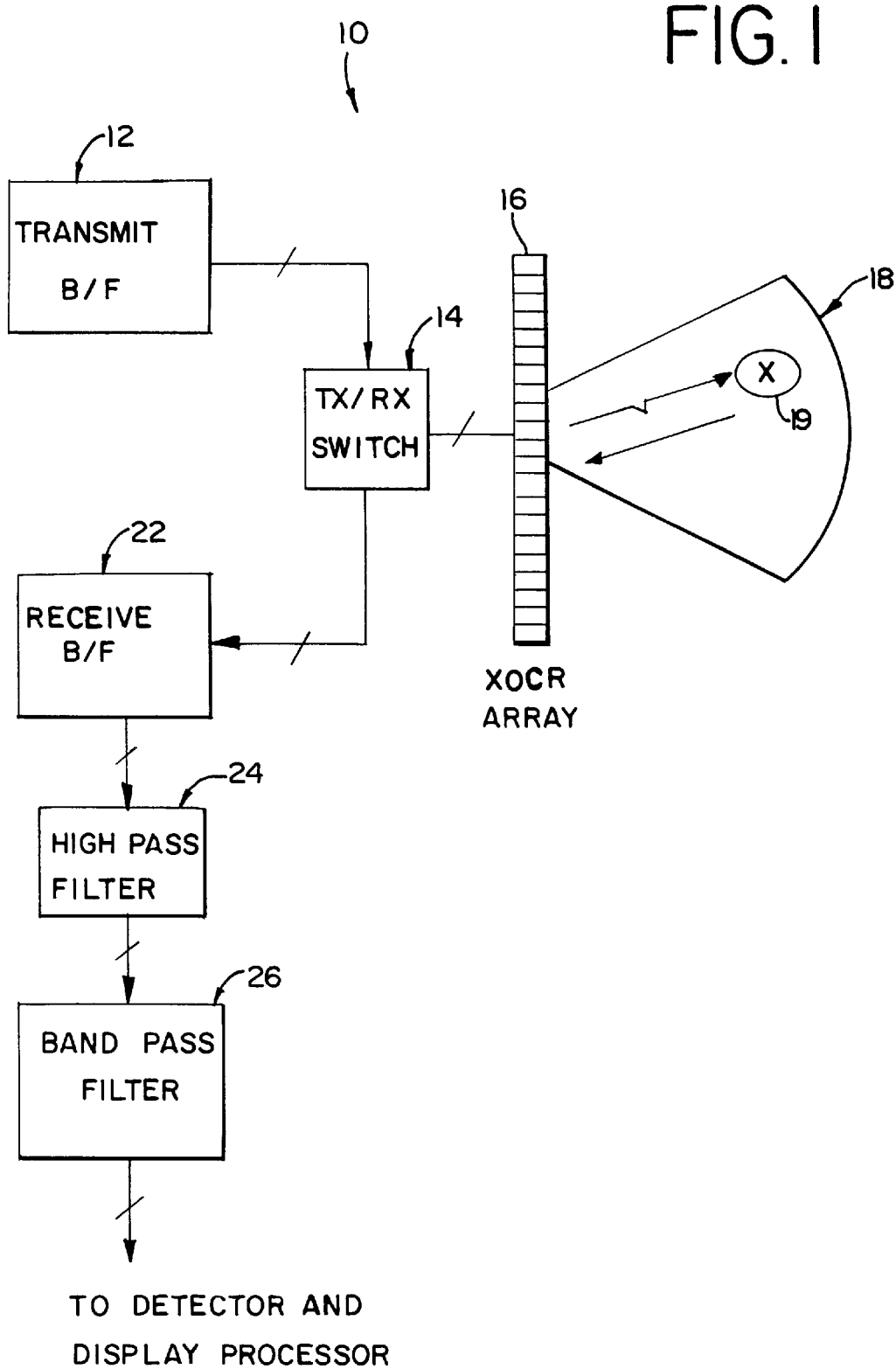
FIG. 1 is a block diagram of an ultrasound system for harmonic imaging.

The preferred embodiments described below are designed to reduce harmonic energy associated with harmonic imaging bands in the transmitted beam, and to provide an improved spectral distribution of fundamental energy in the transmitted beam. Referring now to the figures, and in particular, FIG. 1, an ultrasound system is generally shown at 10. The ultrasound system 10 is configurable to transmit signals with reduced energy at harmonic imaging frequencies and improved spectral distribution of energy at fundamental frequencies. Harmonic frequencies are frequencies associated with non-linear propagation or scattering of the transmit signals, usually at integral harmonics such as second, third, and fourth harmonics. As used herein, harmonic includes second, third, fourth, and other harmonics of the fundamental. Non-linear propagation or scattering results in shifting energy associated with a frequency or frequencies to another frequency or frequencies. As used herein, harmonic shifting may also include energy shifted to subharmonics and fractional harmonics (e.g. ½ or 3/2 of the fundamental).

The system 10 includes a transmit beamformer 12 that supplies high voltage transmit waveforms in a plurality of channels via a TX/RX switch 14 to a transducer array 16. Preferably, the transmit beamformer 12 and the transducer array 16 have a broadband response and are capable of transmitting the maximum allowable acoustic power densities for better signal to noise sensitivity. The transducer array 16, which can be any suitable type, generates an ultrasonic transmit beam in response to the transmit waveforms, and this transmit beam propagates outwardly through the subject 18 being imaged. The transducer 16 frequency response acts as a bandpass filter. Thus, the energies associated with harmonics higher than the harmonic of interest may be removed as the transmit waveform is radiated by the transducer 16.

Ultrasonic energy echoed by the subject 18, such as from a point 19, at the harmonic frequency is received by the transducer array 16 and focused by the receive beamformer 22. Preferably, the transducer 16 and receive beamformer 22 have a broadband response. The focused signal is preferably filtered with a high pass filter 24. The high pass filter attenuates energy associated with fundamental frequencies, which are typically greater than energies associated with harmonic frequencies. Preferably, a bandpass filter 26 further reduces energies associated with frequencies other than the desired harmonic frequencies. Other receive beamformers, both digital and analog, with different or the same filtering structures may be used. The filtered information is detected and displayed as an image by a display processor (not shown).

The harmonic image represents structure within the subject 18. The harmonic signal may be generated by tissue harmonic response or by non-linear contrast agents which may be provided within the subject 18. Tissue harmonic imaging is associated with harmonic energy generation through propagation and scattering of the transmit beam. Contrast agent harmonic imaging is associated with harmonic energy generation through interaction of the fundamental energy with the contrast agent.

Figure 2A:
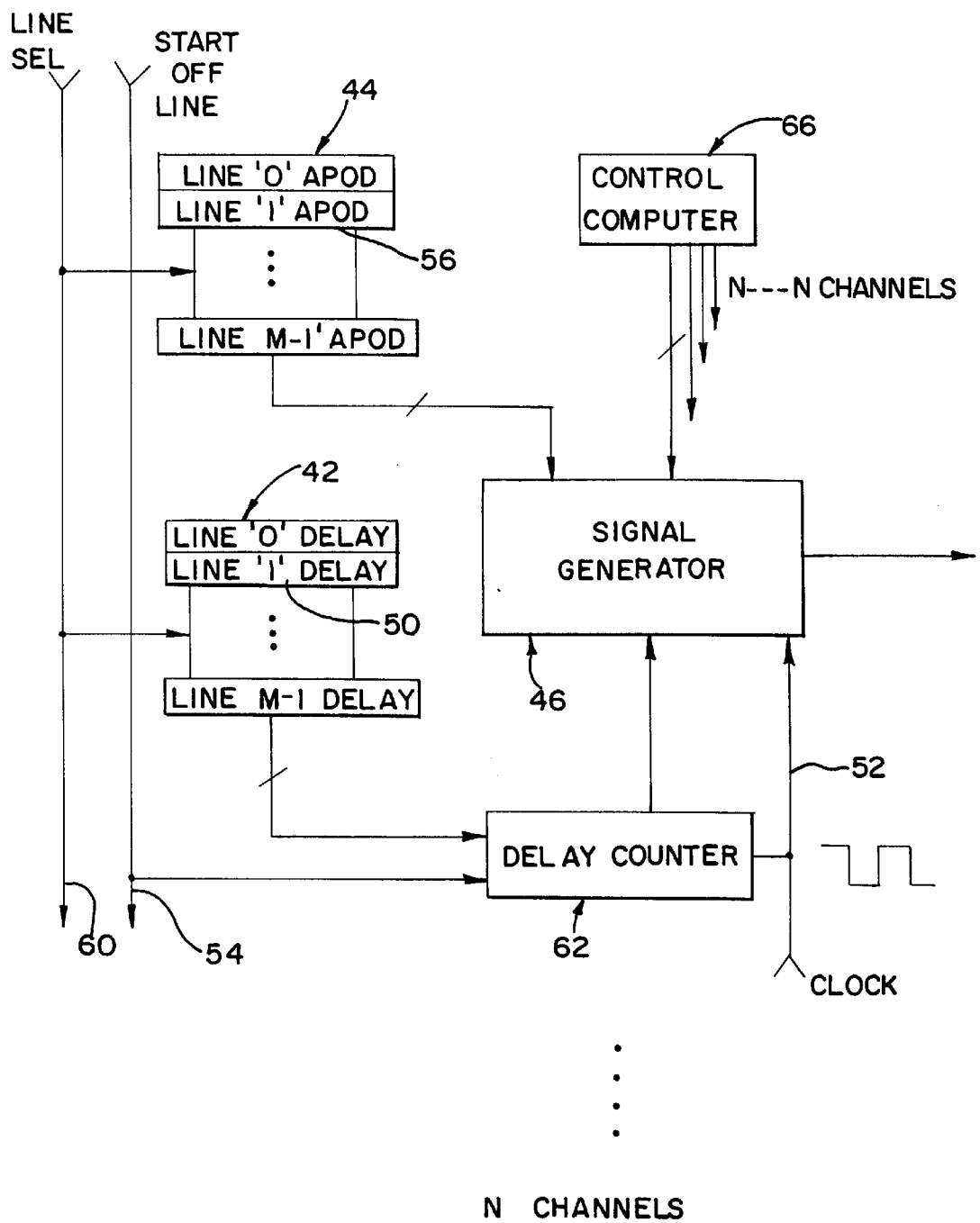
FIG. 2A is a block diagram of a transmit beamformer.

FIG. 2A shows a block diagram of a first preferred embodiment 40 of the transmit beamformer 12 of FIG. 1. As shown in FIG. 2A, the transmit beamformer 40 includes N channels, one for each of the transducers of the transducer array 16 (see FIG. 1). Each channel includes a delay memory 42, an apodization memory 44, a delay counter 62, and a signal generator 46. Any of the various structures may be used for a plurality of channels instead of in a single channel as in the preferred embodiment.

The delay memory 42 includes m delay words 50, one for each possible steering angle or ultrasound transmit scan line. Each delay word 50 of the delay memory 42 corresponds to the time delay for the transmit scan line selected and for the transducer array element connected to the appropriate transmit channel. For example, in the preferred embodiment, the delay word 50 specifies the number of transmit carrier cycles to delay after a start of line signal on line 54 before generation and transmission of the transmit waveform.

The delay memory 42 of FIG. 2A is not required, but reduces memory or control requirements for the signal generator 46. The delay memory 42 eliminates the need to calculate the delay or derive the delay from other parameters as the ultrasound scan line changes angles.

The apodization memory 44 includes m apodization words 56, one for each possible steering angle or ultrasound transmit scan line. Each apodization word 56 of the apodization memory 44 corresponds to an amplitude level or scaling for the particular channel and transmit scan line. Each word 56 is based on apodization formats known in the art.

A computer 66 provides set-up data associated with a selected imaging mode to the signal generator 46 to specify the characteristics of the transmit waveform for the imaging mode. Other embodiments of imaging mode selection are possible. Furthermore, some systems may not provide imaging mode selection.

The signal generator 46 is of a construction known in the art for generating transmit waveforms. For example, the signal generator 46 includes control, timing, waveform generation, scaling, digital to analog conversion, and output driver circuits. Other embodiments are possible, such as the transmit beamformer disclosed in Method and Apparatus for Transmit Beamformer System, U.S. patent application Ser. No. 08/673,410, filed Jul. 15, 1996. Alternative means for waveform generation also include RAM or ROM memory and logic based devices. The complexity and details of the preferred embodiment of the signal generator 46 depend on the number of timing states, apodization levels, and pulse amplitude quantization levels needed to adequately generate the desired transmit waveform.

Figure 2B:
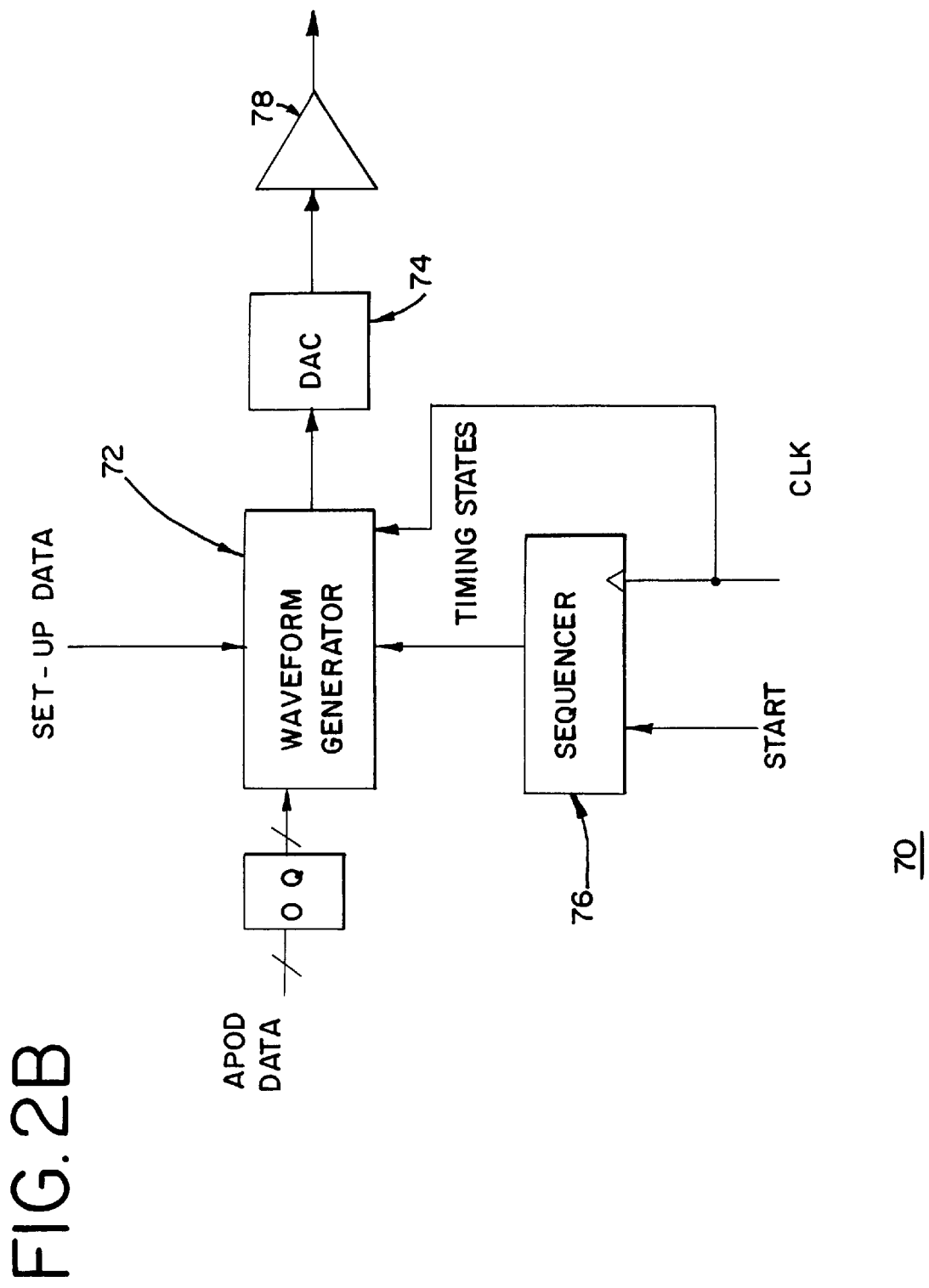
FIG. 2B is a block diagram of a signal generator.

Referring to FIG. 2B, a first preferred embodiment 70 of the signal generator 46 of FIG. 2A is shown. The signal generator 70 includes a timing sequencer 76, waveform generator 72, digital to analog converter (DAC) 74 and a high voltage output driver 78. The waveform generator 72 preferably includes one or more RAM look-up tables for generating amplitude level signals, such as 5 bit signals, based on timing and apodization inputs. The output of the look-up tables is enabled based on the apodization word 56 (see FIG. 2A) and the timing states. The high voltage output driver 78 produces a bi-polar signal, but may produce a uni-polar waveform. The signal generator 70 shown is preferably used for generating transmit waveforms designed using amplitude modulation as discussed below, but may be used for other transmit waveforms.

In an alternative construction, a plurality of resistors and switches are used instead of the DAC 74 to weight or further provide generation of the transmit waveform at different amplitude levels. Furthermore, the waveform generator 72, such as multi-level switched or another analog device, may be capable of producing signals with varying amplitudes based on a stored waveform or other inputs without the DAC 74. In other alternative constructions for bi-polar transmitters, more than one DAC 74 is used for push-pull operation. In yet other alternative constructions, any of the timing sequencer 76, waveform generator 72, and other logic and control structures are shared by more than one channel.

Referring to FIGS. 2A and 2B, the apodization memory 44 is not required, but allows more precise focusing and amplitude control. Without the apodization capability and associated memory 44, the functions of the waveform generator 72 and DAC 74 are simplified. In this case, the signal generator 70 outputs amplitude levels corresponding to a constant apodization weighting.

Referring to FIG. 2A, in use, control data specifying the channel timing delay words 50, apodization words 56 and any other required set-up data is provided to the transmit beamformer 40. Other set-up data is preferably provided by the computer 66, preferably including parameters, such as a carrier frequency, a bandwidth, and other information as a function of possible timing states and apodization levels. In alternative constructions, any of the control data may be provided by alternative structures.

Based on the control data, each channel responds to a scan line selection signal on line 60 by loading the words 50 and 56 for the selected scan line. The word 50 from the delay memory 42 is loaded into the delay counter 62. Since the delay word 50 is preferably specified in fractions of a carrier cycle, the delay word 50 is used to select a finely quantized timing state corresponding to the clock phase. The delay counter 62 responds to a start of scan line signal on the line 54 by incrementing or decrementing the stored value with each cycle of the clock on the line 52. When the counter 62 counts to zero, the next cycle initiates a start signal for waveform generation. Referring to FIG. 2B, the start signal is received by the sequencer 76. The sequencer 76 generates the appropriate timing states for amplitude modulated pulse generation by the waveform generator 72.

Referring to FIGS. 2A and 2B, the signal generator 46 also receives the apodization word 56 from the apodization memory 44. The apodization word 56 is preferably used by the waveform generator 72 as a scale factor for the generated waveform. Thus, the apodization word is used to scale the waveform amplitude levels provided to the DAC 74 in addition to the amplitude modulation discussed below.

Based on the set-up data, apodization, and sequencer state information, the waveform generator 72 produces an amplitude modulated waveform for transmission. The preferred signal generator 70 outputs a clocked sequence of multiple amplitude levels during the active portion of the transmit pulse or pulses generation. The clocked sequence is preferably coarsely sampled, such as 4 or 8 samples per cycle. The sequencer 76 provides timing states for generating successive amplitude levels in the pulse train, or amplitude modulated transmit waveform. Preferably, the amplitude modulated transmit waveform includes at least two carrier cycles. Other sampling rates may be used as discussed below. The amplitude levels of each pulse output from the waveform generator 72 are represented by multiple bit words using binary code, thermometer code, gray-code, specially weighted code or a combination of the codes, as known in the art. The preferred amplitude levels are a function of amplitude shaping and apodization, as discussed below.

The encoded output levels are converted to analog by the DAC 74 and amplified by the output driver 78. Preferably, the output power of the output driver 78 is regulated by changing the voltage or current amplification of the output driver 78 for every channel the same factor. Apodization and waveform shaping control for each channel preferably involves changing the waveform amplitude prior to the DAC 74. The output of the output driver 78 is the transmit waveform discussed above and is applied to the respective transducer 16 via the TX/RX switch 14 (see FIG. 1). Thus, a uni-polar or bi-polar high voltage transmit waveform is generated. When the pulse train for the desired transmit waveform is complete, the sequencer 76 returns to an idle state until the next start signal is received.

In an alternative method, the transmit waveform is generated without applying apodization scaling within the waveform generator 72. The required apodization scaling is multiplied with the output from the waveform generator 72. The multiplication is performed using a multiplying DAC 74 or other structures.

The amplitude shape of the transmit waveform enhances insonification for harmonic imaging. The computer 66, either in real-time or as part of the set-up, provides information for generating any of various waveforms for use with signal generators 46 of various complexity. The waveforms are shaped to suppress ultrasonic energy in a wide pass band centered at the harmonic frequency of the fundamental center frequency of the transmit waveform.

Figure 3A:
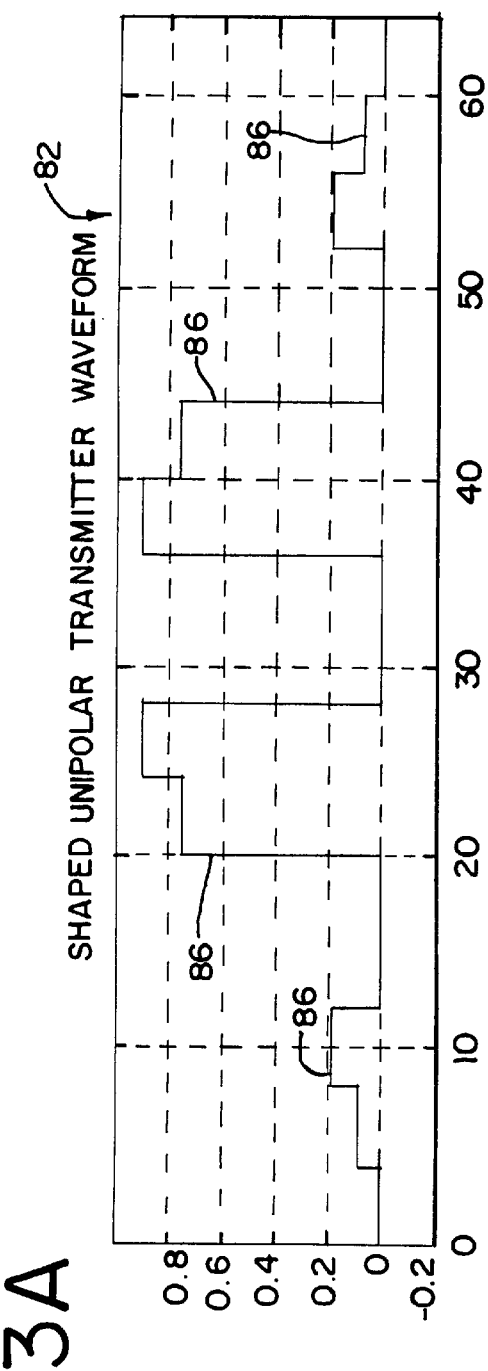
FIG. 3A is a graphical representation of a transmit waveform.
Figure 3B:
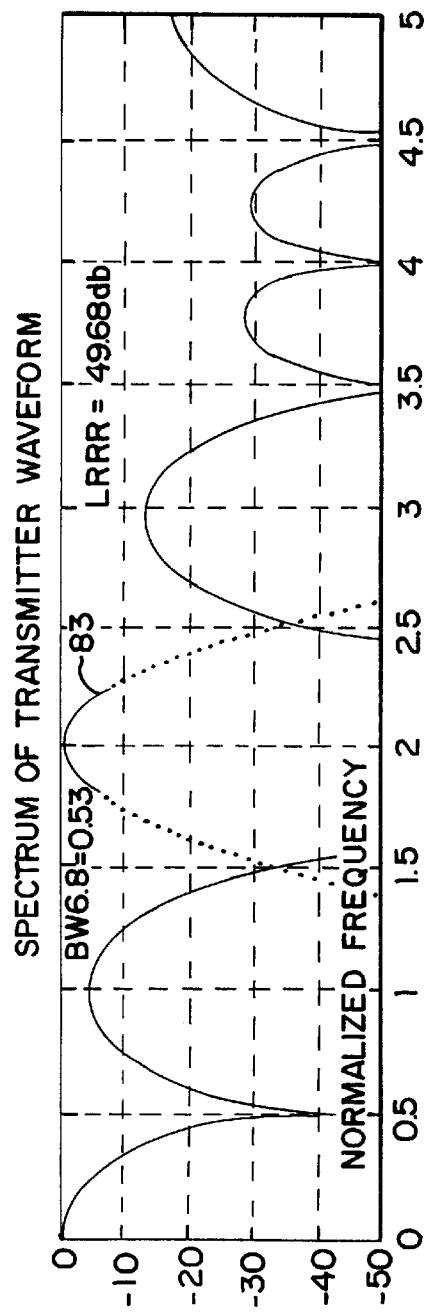
FIG. 3B is a graphical representation of a spectrum associated with the transmit waveform of FIG. 3A.

The suppressed harmonic transmission allows the system to distinguish harmonic echoes (tissue or contrast agent based) from linear echoes. A calculation demonstrating the transmit waveform corruption of energies in the harmonic frequencies is a Linear Response Rejection Ratio (LRRR). The LRRR is the ratio of residual power of the transmit waveform spectrum in the desired harmonic band, such as a band centered around the second order harmonic, to the power of the transmit waveform spectrum in the corresponding fundamental band. A matched weighting filter, shifted as appropriate for harmonic and fundamental power calculation, is applied to calculate the powers. Conventional rectangular wave transmitters typically generate transmit waveforms with less than 35 dB LRRR. Optimum shaped transmit waveforms for harmonic imaging have greater than 35 dB LRRR. For example, the transmit waveform 82 shown in FIG. 3A has an LRRR of approximately 49.7 dB, as shown in FIG. 3B. The LRRR calculation is based on the weighting filter response 83 (dotted line) shown in FIG. 3B. Transmit waveforms with less than 35 dB LRRR may be used for harmonic imaging, but may result in more corruption of the desired harmonic signal.

The waveforms are preferably shaped to provide optimum fundamental band efficiency. The efficiency of a waveform is a relative measure of the spectral energy in a weighted band around the fundamental center frequency when the peak is normalized to a given value. Referring to FIG. 2A, for the optimum sensitivity in tissue harmonic imaging, the transmit beamformer 40 transmits at or near the maximum allowed acoustic power density. For harmonic imaging of contrast agents, the power levels may be reduced to avoid destruction of the contrast agent. Thus, efficiency is one factor to be considered in designing and generating the waveform.

The complexity of the waveform is another such factor. Waveforms requiring only coarse sampling, fewer amplitude levels and less amplitude quantization accuracy in the DAC processing require less complex and costly hardware to generate. Since a plurality of signal generators 46 are typically used, the cost difference between signal generators 46 is an important consideration.

Figure 5A:
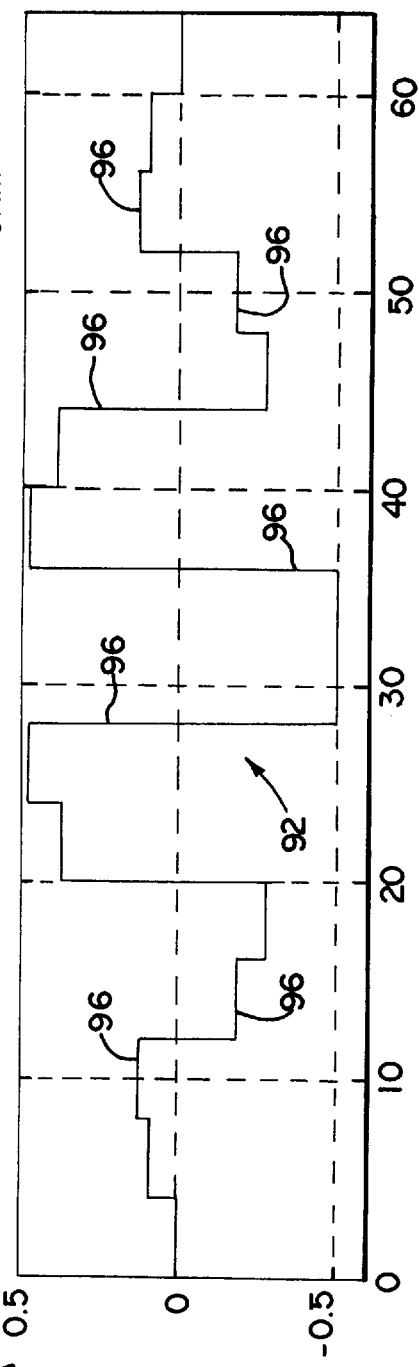
FIG. 5A is a graphical representation of a transmit waveform.

The transmit waveforms are either uni-polar or bi-polar. Referring to FIGS. 3A and 5A, a uni-polar transmit waveform 82 is shown (FIG. 3A), and a bi-polar transmit waveform 92 is shown (FIG. 5A). The transmit waveforms 82 and 92 include one or more pulses 86 and 96. The pulses 86 and 96 correspond to intervals along the time axis where the amplitude starts at zero or another value and then returns to zero or another value. Typically, each pulse corresponds to a sample. For example, the transmit waveforms 82 and 92 in FIGS. 3A and 5A are sampled 4 times per carrier cycle. Other sample rates may be used, such as 8. Two or more pulses 86 and 96 may be adjacent another pulse 86 or 96 along the time axis. Each pulse 86 and 96 is preferably stepped or rectangular. Stepped and rectangular pulses may include curved or other shapes. Sinusoidal waveforms or pulses of other shapes may also be used, but stepped or rectangular waveforms typically require less complex transmit beamformers 12 (see FIG. 1).

Preferably, the stepped waveforms have at least two positive or negative amplitude levels or a combination of a plurality of positive and negative amplitude levels to allow shaping as discussed below. However, rectangular waveforms with only two amplitude levels (on/off) for uni-polar or three amplitude levels for bi-polar (positive/off/negative) may be used as discussed below.

The transmit waveforms 82 and 92 preferably have gradually increasing amplitudes followed by gradually decreasing amplitudes for each pulse 86 and 96 or from pulse to pulse, but other shapes are possible. For example, the transmit waveform corresponds to a Gaussian or Hamming envelope shape. The gradually increasing and decreasing amplitude, or envelope, corresponds to at least one step between two amplitude values, such as zero and full power. For greater numbers of amplitude levels, the transition from the zero amplitude to the maximum amplitude may be more gradual. The gradually increasing and decreasing amplitude shape reduces the energy in the spectral sidelobes at the second harmonic frequencies. Other shapes associated with other harmonics may be used.

The transmit waveforms are conceptualized or represented by two methods. First, the transmit waveforms are represented as sampled, modulated signals, as symbolically shown in FIG. 4A. The modulated signal or transmit waveform is the product of carrier and envelope components. Second, the transmit waveforms are represented as base waveforms, such as a modulated bi-polar waveform, summed with an off-set waveform, as symbolically shown in FIG. 4B.

Referring to FIGS. 3 and 5, for modulation, the sampled carrier waveform 80 and 90 and the sampled sampled envelope waveform 84 and 94 are optimized separately. For example, the sampled carrier waveform 90 is represented from a bi-polar carrier ($\cos(2\pi t/T)$ (see FIG. 5C), where t is the time and T is the period of the fundamental carrier frequency), but a uni-polar carrier as represented from ($[1+\cos(2\pi t/T_c)]$)(see the sampled carrier waveform 90 shown in FIG. 3C) is possible. Other representations of the sampled carrier waveform 90 may be used. The sampled carrier waveform 90 determines the center fundamental frequency and the relative magnitude of the spectral energy at the fundamental and odd harmonic frequencies. The center fundamental frequency is preferably within 1–15 MHz, but other frequencies may be used. The sampled carrier waveform 90 is also associated with the average to peak ratio or the efficiency of the transmit waveform.

Figure 5B:
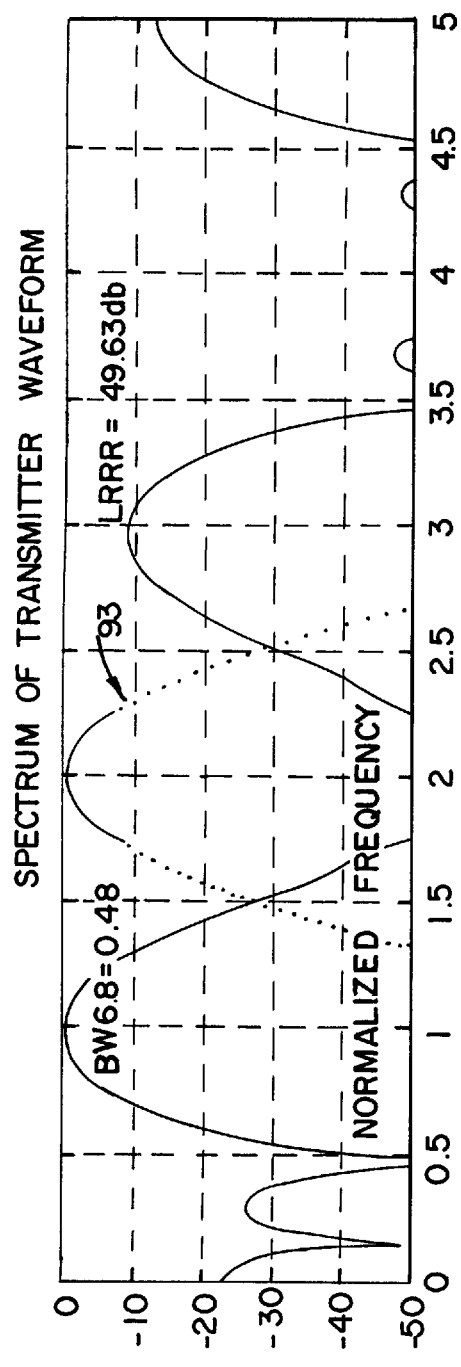
FIG. 5B is a graphical representation of a spectrum associated with the transmit waveform of FIG. 3A.
Figure 5C:
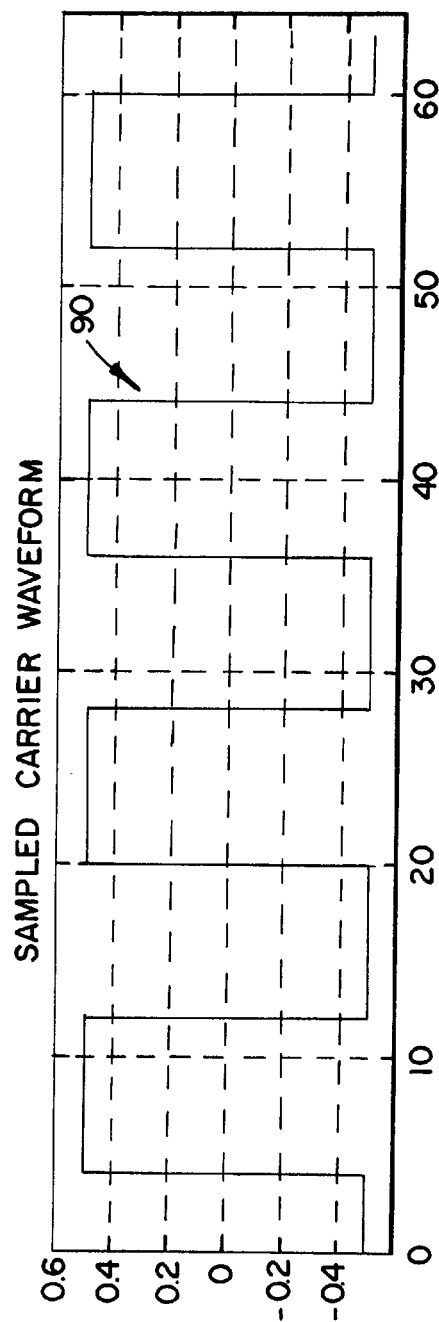
FIG. 5C is a graphical representation of a carrier waveform.

The sampled envelope waveform 94 determines the fundamental main lobe shape, the bandwidth, and sidelobe shape around the odd harmonics of the carrier. The amplitude shape of the sampled envelope waveform 94 limits the amplitude of the spectrum of the transmit waveform 92 in the even harmonic bands, such as the second order harmonic band. Referring to FIG. 5B, the spectrum associated with the transmit waveform 92 demonstrates the reduced energy for the second order harmonic band. To limit the even harmonic frequency bands, the sampled envelope waveform 94 preferably gradually increases to a maximum value and then gradually decreases. For example, the sampled envelope waveform 94 shown provides a rise from a zero amplitude to a maximum amplitude and a fall from the maximum amplitude to the zero amplitude. Other shapes, such as Gaussian or varying slope ramps, may be used. The sampled envelope waveform 94 is also associated with the efficiency of the transmit waveform.

The sampled envelope waveform 94 is preferably obtained by even sampling of a Hamming envelope or similar function. The envelope function is sampled at a rate represented by T/4, where T is the period of the sampled carrier waveform 90. The sampled even Hamming envelope function is represented by the equation:

$$e(t)=\Sigma_k[0.54+0.46\cos(2\pi(k+\tfrac{1}{2})\ (T/4T_h))]\mathrm{rect}[4(t+(k+\tfrac{1}{2})T/4)/T],$$

where t represents time, $T_h$ is the envelope width, k=0,+/1,+/−2 . . . , for k such that $$|k+\frac{1}{2}|<=2T_h/T.$$

Other envelope functions, such as a Gaussian function, may be used.

The parameter, $T_h$, determines the bandwidth of the fundamental frequency lobe as discussed above, as well as aspects of the sidelobe structure associated with each harmonic of the carrier frequency. By varying $T_h$, the number of pulses 96 in the transmit waveform 92 is varied. A larger $T_h$ (wider envelope) narrows the bandwidth of the fundamental frequency lobe. However, narrowing the bandwidth also reduces spatial resolution.

Figure 5D:
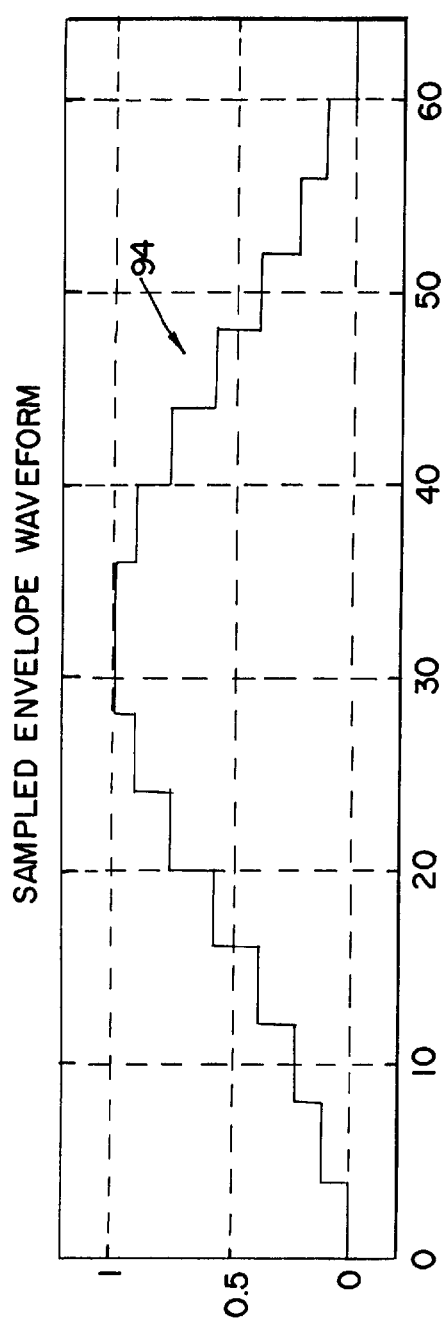
FIG. 5D is a graphical representation of an envelope waveform.

The carrier waveform 90 is modulated with the sampled envelope waveform 94. For example, the preferred bi-polar transmit waveform 92 is shown in FIG. 5A. In this example, the sampled carrier waveform 90 has a center frequency normalized to 1 Hz. Other center frequencies, such as within the 1–15 MHz range, are possible. The transmit waveform 92 is the product of the sampled carrier waveform 90 (FIG. 5C) and the sampled envelope waveform 94 (FIG. 5D). The transmit waveform 92 includes a plurality of amplitude modulated pulses 96 corresponding to the sampled carrier waveform 90, but other pulses 96, such as square, stepped, or other rectangular pulses, may be used. The amplitude from pulse 96 to pulse 96 corresponds to the sampled envelope waveform 94. Thus, the amplitude levels of the outer pulses 96 are reduced. The spectrum associated with the transmit waveform 92 is shown in FIG. 5B. The LRRR calculation shown is based on the weighting filter response 93 (dotted line) shown in FIG. 5B.

Referring to FIG. 3, a preferred uni-polar transmit waveform 82 is shown. The spectrum associated with the transmit waveform 82 is demonstrated in FIG. 3B. The carrier and envelope waveforms 80 and 84 are shown in FIGS. 3C and 3D, respectively. The envelope waveform 84 is similar to the sampled envelope waveform 94 shown in FIG. 5D. The carrier waveform 80 is uni-polar. The product of the carrier waveform 80 and the envelope waveform 84 is also uni-polar. As compared to the bi-polar transmit waveform 92 shown in FIG. 5, the uni-polar transmit waveform 82 shown in FIG. 3 is associated with fewer pulses 86 and fewer amplitude levels since one or more samples of the carrier waveform 80 is zero. Due to the fewer amplitude levels, the quantization requirements of the DAC 74 (see FIG. 2B) are reduced. Other numbers of amplitude levels, greater or less than 16, may be used for either bi-polar or uni-polar transmit waveforms.

The transmit waveforms are preferably sampled at a rate corresponding to multiples of the carrier frequency. For lower sample rates, less complex hardware is required. For example, the bi-polar transmit waveform 92 shown in FIG. 5A is sampled four times during the period, T, of the sampled carrier waveform 90. The sample rate is optimized separately for the carrier and envelope waveforms 90 and 94. Preferably, the sampling rate associated with the sampled envelope waveform 94 is a multiple of the sample rate associated with the sampled carrier waveform 90. For example, the sampled carrier waveform 90 is sampled two times during the period, and the sampled envelope waveform 94 is sampled four times during the period. Refer to FIG. 6 for another example (carrier and envelope waveforms 100 and 104 sampled 4 times and 1 time in the carrier period, respectively). These sampling rates represent coarse sampling, requiring less complex hardware, as discussed above. If only the second harmonic band of frequencies is used for imaging, the coarsely sampled, such as T/8 or T/4, rectangular or stepped transmit waveforms have similar efficiency and harmonic rejection as more complex or frequently sampled waveforms. Other sample rates and the associated possible amplitude changes may be used, such as high sample rates used for generating complex waveforms.

Referring to FIG. 5, preferably, the sampled carrier waveform 90 is sampled for even-phasing with respect to the center of the transmit waveform 92. By sampling the sampled envelope waveform 94 with an even sampling phase, the phases of the sampled envelope waveform 94 and the sampled carrier waveform 90 are aligned (even sampling phase). The symmetry achieved by using even sampling phase reduces the number of amplitude levels and the sampling rate associated with the transmit waveform 92. Thus, a less complex transmit beamformer 12 (see FIG. 1) is required. Even sampling also increases the average to peak ratio of spectral energy for greater efficiency using a peak limited transmit beamformer (see FIG. 1). The sampling phases of the carrier and envelope waveforms 90 and 94 may be different. Alternative transmit waveforms 92 with different sampling rates for the carrier and envelope waveforms are also possible.

Figure 6A:
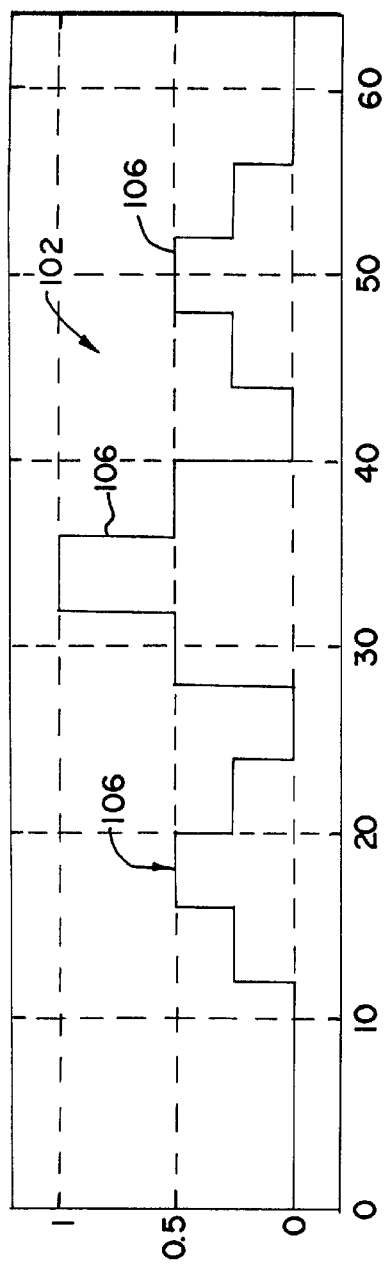
FIG. 6A is a graphical representation of a transmit waveform.
Figure 6B:
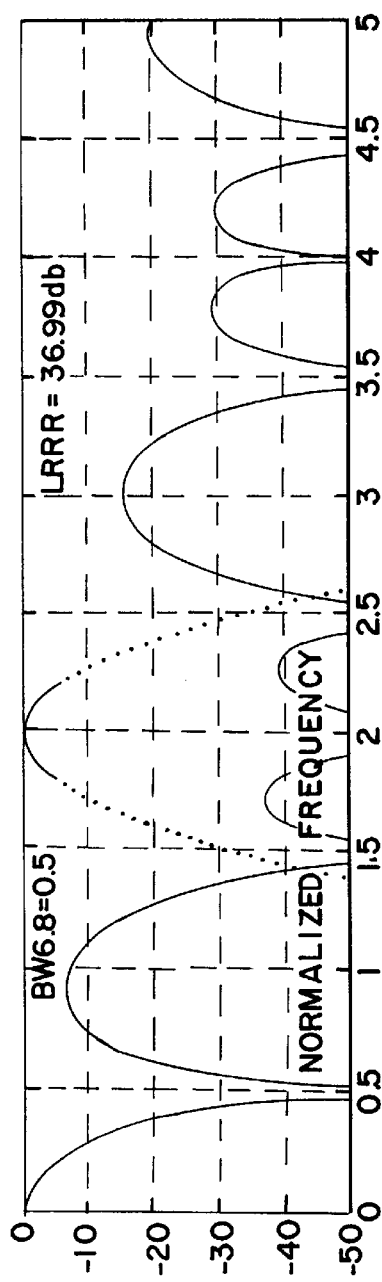
FIG. 6B is a graphical representation of a spectrum associated with the transmit waveform of FIG. 3A.
Figure 6C:
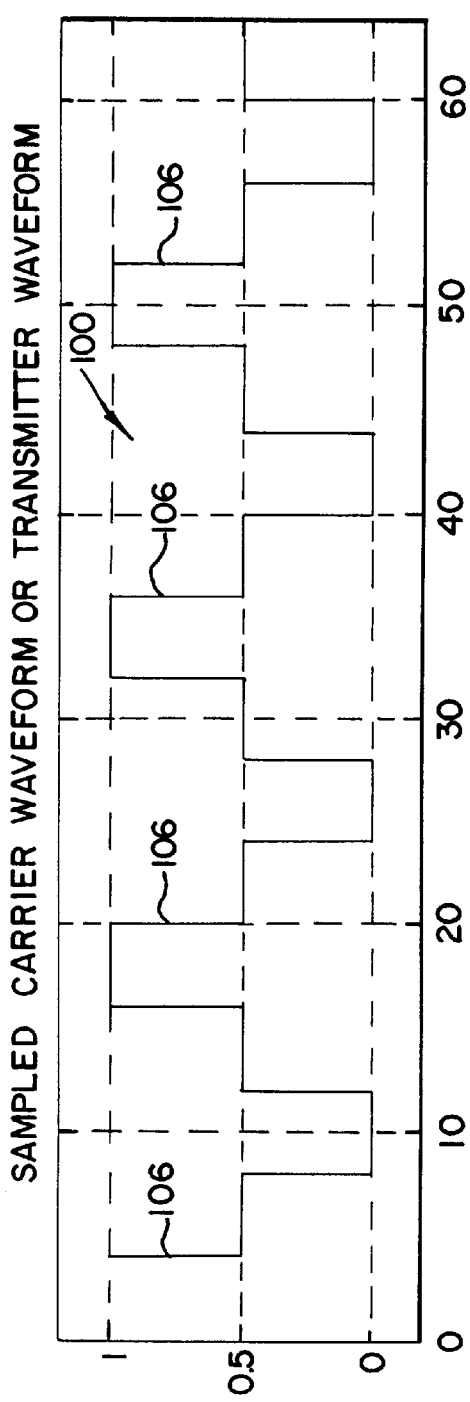
FIG. 6C is a graphical representation of a carrier or transmit waveform.
Figure 6D:
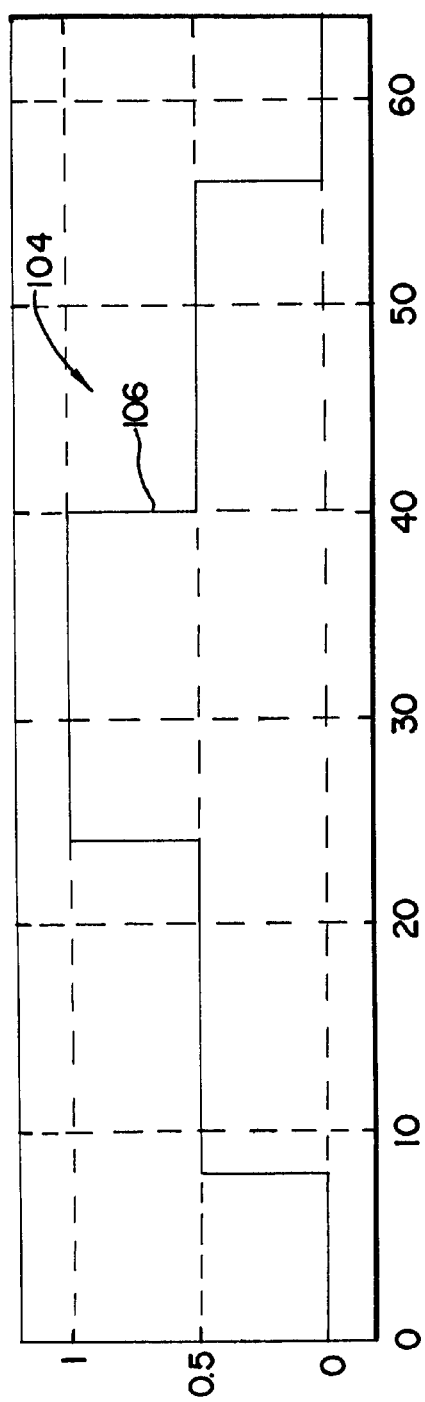
FIG. 6D is a graphical representation of an envelope waveform.
Figure 7A:
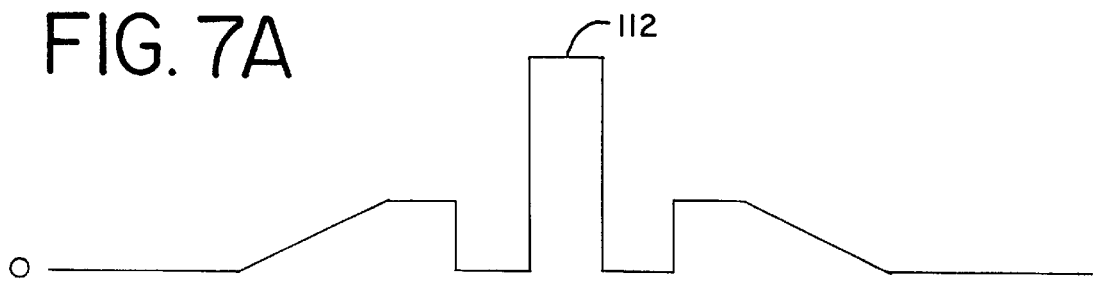
FIG. 7A is a graphical representation of a transmit waveform.
Figure 7B:
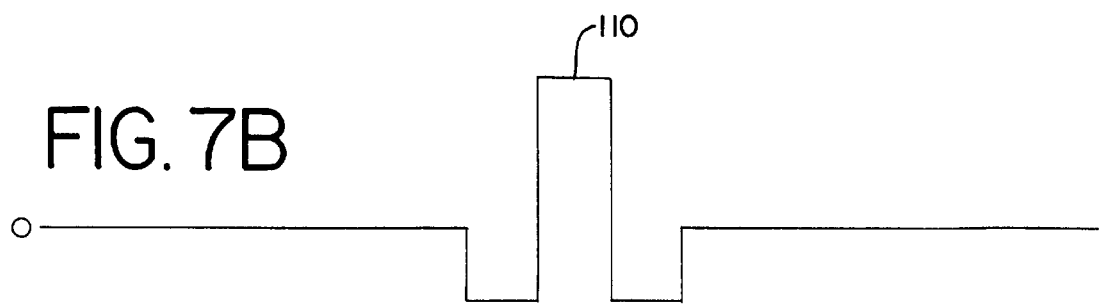
FIG. 7B is a graphical representation of a bi-polar waveform.
Figure 7C:
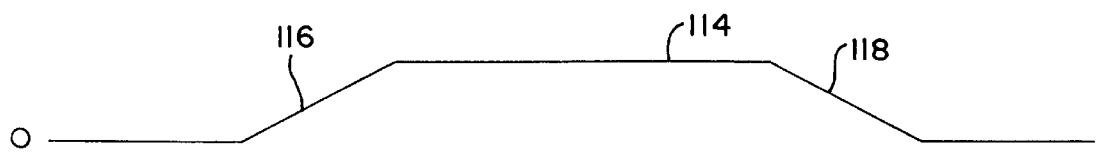
FIG. 7C is a graphical representation of an off-set waveform.
Figure 7D:
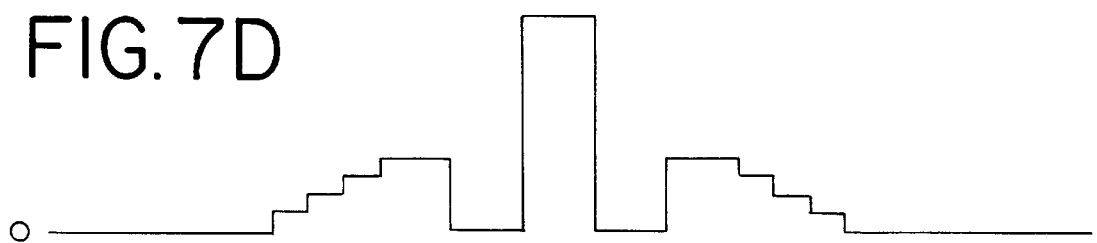
FIG. 7D is a graphical representation of a transmit waveform.
Figure 7E:
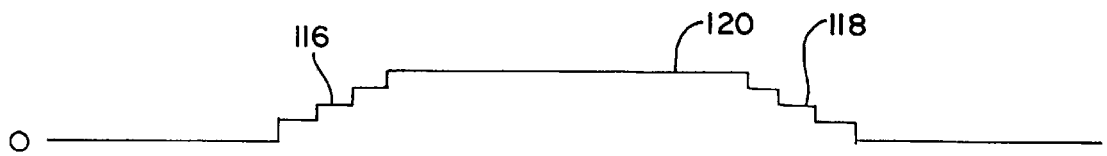
FIG. 7E is a graphical representation of an off-set waveform.

As a further alternative and as referenced above, one or more pulses associated with a transmit waveform are amplitude shaped or modulated. Preferably and as shown in FIG. 6C, the amplitude associated with each pulse 106 gradually increases to a maximum level and gradually decreases from the maximum level. For example, the uni-polar transmit waveform 100, based on sampled and phased rectangular carrier waveform and an envelope waveform similar to the envelope waveform 104 shown in FIG. 6D, is generated and transmitted after applying a rectangular window function. Compared to a uniform amplitude rectangular pulse transmit waveform, the windowed transmit waveform 100 is associated with reduced energy in the second order harmonic band. Thus, the transmit waveform 100 corresponds to improved LRRR. Bi-polar transmit waveforms with amplitude modulated pulses of this type are also possible.

Furthermore, the amplitude associated with the windowed transmit waveform 100 from pulse 106 to pulse 106 is preferably shaped. The windowed transmit waveform 100 is used as a carrier waveform and modulated with the envelope waveform 104 shown in FIG. 6D, resulting in the transmit waveform 102 shown in FIG. 6A. Thus, control of the energies transmitted at second order harmonic frequencies is optimized by shaping each pulse 106 and the transmit waveform 102 from pulse 106 to pulse 106 (shaping the burst).

As an alternative to generating the carrier or transmit waveform 100 shown in FIG. 6C, two waveform generators capable of producing DC switched (ON/OFF) rectangular waves are used. First and second uniform amplitude rectangular waves, two or three cycles in duration, are generated. The first waveform is shifted 90 degrees out of phase at the fundamental frequency (quarter cycle delay) from the second waveform. The first and second waveforms are summed prior to transmission or in the acoustic domain as discussed below.

Figure 4A:
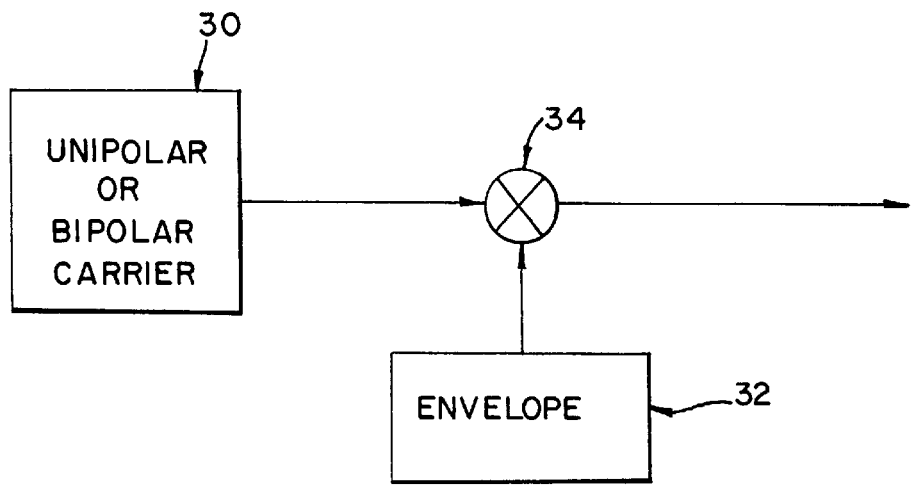
FIG. 4A is a block diagram showing modulation.

The conceptualization of the transmit waveforms through modulation, as demonstrated by FIG. 4A, is used to design the transmit waveforms. As discussed above, the signal generator 46 (see FIG. 2A) generates the transmit waveform. Alternatively, a signal generator 30 provides a carrier waveform to a multiplier 34. The multiplier 34 also receives an envelope waveform from a second signal generator 32. The signal generators 30 and 32 are any structure capable of generating the desired waveforms, such as an oscillator, a DC switch or memory devices. The carrier and envelope waveforms are multiplied (modulated) to produce the transmit waveform.

Figure 4B:
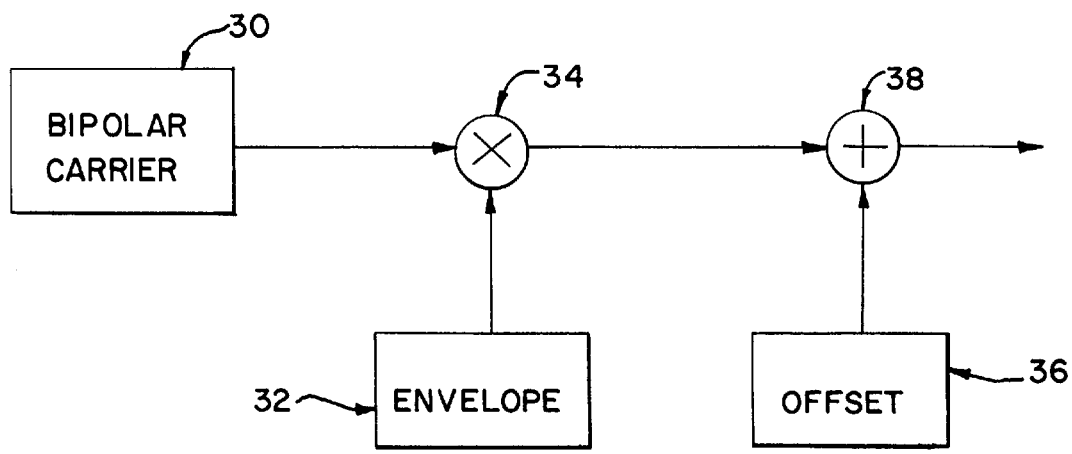
FIG. 4B is a block diagram showing off-set addition.

Other than modulation with an envelope waveform, unipolar transmit waveforms are also conceptualized and represented as a combination of a bi-polar waveform with an off-set waveform (DC component). For example, the transmit waveform 82 is represented as a combination of a bi-polar waveform and an off-set waveform and is characterized by a gradually increasing and decreasing amplitude, or envelope. Referring to FIG. 4B, the bi-polar waveform is further conceptualized as a modulated waveform, but unmodulated waveforms may be used. The bi-polar waveform is coarsely sampled with a uniform amplitude, but other sample rates and amplitude shaping or envelopes may be used. Referring to FIG. 7, the amplitudes associated with the off-set waveform 114 are of sufficient positive or negative values to off-set any negative or positive amplitude, respectively, associated with the bi-polar waveform 110. By selecting off-set waveforms 114 with mostly low frequency energy (long duration and gradually varying amplitude), the amount of transmitted energy in the harmonic frequencies is reduced. By summing the off-set waveform 114 with the bi-polar waveform 110, the transmit waveform 112 is created.

The off-set waveform changes in amplitude linearly or in steps (off-set waveforms 114 and 120, respectively) and is generated by analog or digital devices. Preferably, the off-set waveform is a stepped waveform including gradually increasing and decreasing amplitudes 116 and 118 for providing improved second order harmonic spectrums. Preferably, the stepped off-set waveform 120 is sampled at T/4 of the carrier or finer. Other amplitude shapes for the reduction of energies associated with the same or different harmonics are possible.

Figure 8:
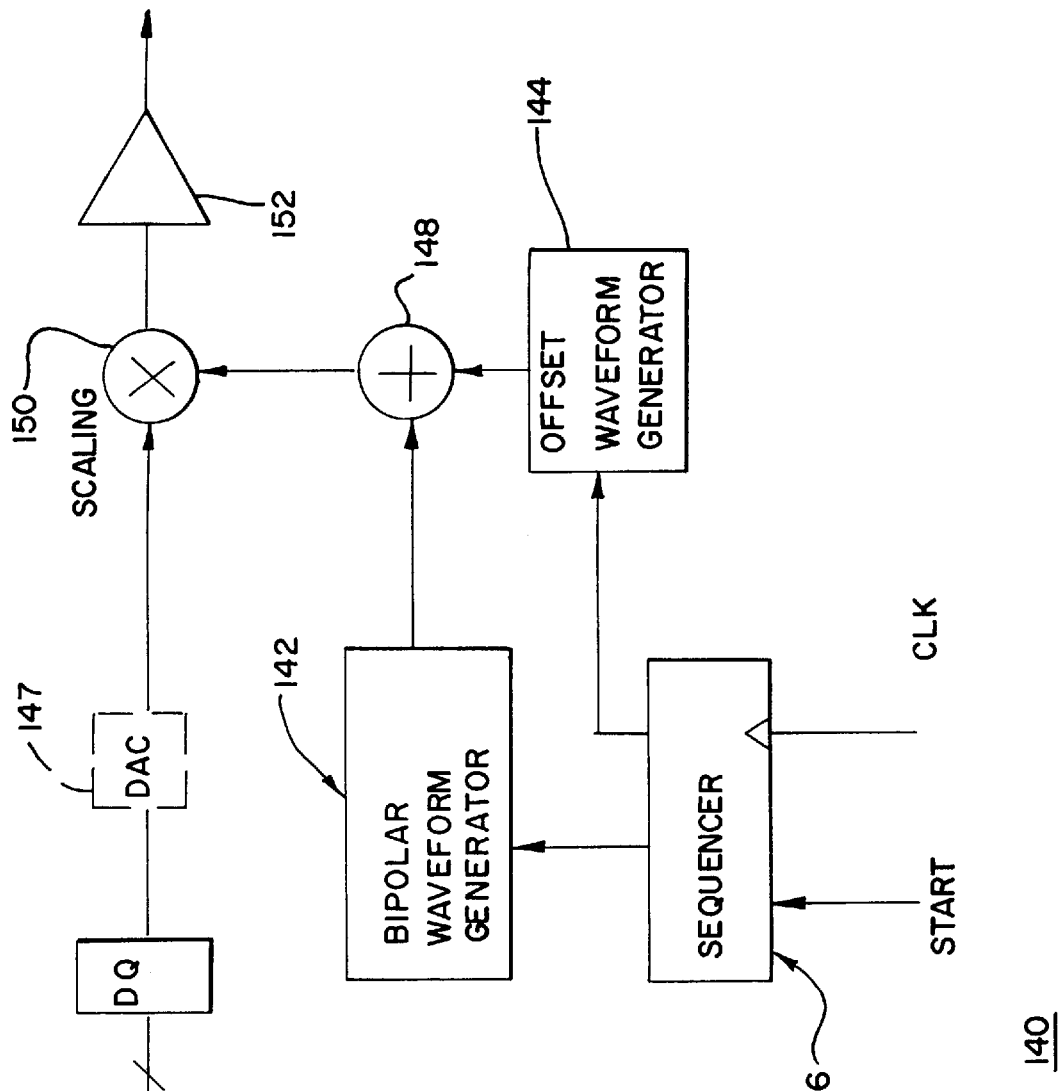
FIG. 8 is a block diagram of a signal generator.

The uni-polar transmit waveforms discussed above, such as the off-set conceptualized transmit waveforms, are generated by the waveform generator 72 shown in FIG. 2B. However, other waveform generation structures are possible and may not require a stepped transmit waveform. For example, an alternative and second preferred embodiment of the signal generator 46 (see FIG. 2A) is shown generally at 140 in FIG. 8. The signal generator 140 includes a waveform generator 142 for generating the bi-polar waveform, an off-set waveform generator 144, a sequencer 146, a summer 148, and a scaler 150.

The summer 148 and the scaler 150 are either digital or analog devices. The sequencer 146 provides timing state information as discussed above to the waveform and off-set waveform generators 142 and 144. The bi-polar waveform generator 142 is preferably a logic, DC switch or any other device capable of generating a bi-polar waveform with at least three amplitude levels. Waveform generators capable of generating bi-polar waveforms with more amplitude levels may be used. The off-set waveform generator 144 is a digital or an analog device. If the off-set waveform generator 144 is a digital device, a stepped signal is generated based on coding, such as discussed above. The summer 148 adds the off-set waveform to the bi-polar waveform. The output of the summer 148 is scaled by scaler 150 using either digital or analog scaling in accordance with apodization. If the output of the scaler 150 is digital, then the output is converted to an analog signal. An analog signal is provided to an uni-polar output driver 152 for amplification.

Referring to FIG. 2A, any of the transmit waveforms discussed above or other transmit waveforms for harmonic imaging are generated by the transmit beamformer 40. The transmit waveforms are generated as calculations based on the concepts discussed above. Alternatively, the transmit waveforms are developed through experimentation. In either case, the signal generator 46 generates the transmit waveform as a function of the capabilities of the transmit beamformer 40. The transmit waveforms are generated based on real time calculations or based on earlier off-line development of the transmit waveform stored in the computer 66 or signal generator 46.

As an alternative embodiment, one or more filters may be added to the transmit beamformer 40 of FIG. 2. A filter, such as a digital, low pass filter, filters the output of the waveform generator. The filter may also comprise an analog filter. The output of the waveform generator can be any of the various waveforms discussed above, such as the bi-polar waveforms, or other waveforms. The filter reduces the transmitted energy associated with various harmonic frequencies, such as at least by 30 dB with respect to the fundamental frequencies. Thus, the generated waveform as discussed above and the filter, in combination, reduce the transmitted energy associated with harmonic frequencies. As a further alternative, the filter, such as a low pass analog filter, filters the output of the DAC or the amplifier. The filtering of the waveform to reduce energies associated with harmonic frequencies is discussed in U.S. Application No. (unassigned—Attorney Docket No. 5050/221) for Ultrasonic Contrast Agent Imaging System and Method (a continuation-in-part of U.S. application Ser. No. 08/642, 528), assigned to the assignee of the present invention and filed concurrently herewith, the disclosure of which is hereby incorporated by reference.

As yet another alternative embodiment, the transmit waveforms discussed above may be pulse width modulated. As disclosed in U.S. Application No. (unassigned—Attorney Docket No. 5050/218) for Ultrasound Imaging Method and Apparatus For Generating Pulse Width Modulated Waveforms With Reduced Harmonic Response, assigned to the assignee of the present invention and filed concurrently herewith, the disclosure of which is hereby incorporated by reference, the duration of each pulse within a burst is selected to reduce the energy transmitted at harmonic frequencies. In particular, the duration of one or more pulses is different than other pulses within the burst. Preferably, the width of the pulses within the burst gradually increase and then decrease, but other duration patterns may be used. To generate pulses with different widths, the sequence of values in the delay words 50 (see FIG. 2) enable each pulse at a set duration. Alternatively, the waveform generator, based on control signals or storing the waveform in memory, generates the waveform after the entire burst is enabled by the appropriate delay word 50.

As yet another alternative embodiment, the transmit waveforms discussed above may be shaped as a function of summation of the waveforms in the acoustic domain. As disclosed in U.S. Application No. (unassigned—Attorney Docket No. 5050/219) for Ultrasound Imaging Method And System For Harmonic Imaging Pulse Shaping In The Acoustic Domain assigned to the assignee of the present invention and filed concurrently herewith, the disclosure of which is hereby incorporated by reference, the transmit waveform associated with a first transducer element or elements is shaped relative to a second waveform associated with a second transducer element or elements. For example, the first waveform (1) is delayed by a fraction of a cycle or one or more cycles, (2) is adjusted in amplitude, (3) is transmitted for a different number of cycles or (4) any combination of two or all three of (1), (2), and (3) relative to the second waveform. The first and second waveforms are focused at a point and transmitted. The transmitted waveforms sum in the acoustic domain at the point to form the desired waveform for reduction of energies transmitted in the harmonic frequencies. Preferably, the desired summed waveform corresponds to an amplitude or envelope that rises gradually to a maximum value and decreases gradually from the maximum value.

As an example of generating transmitted waveforms as a function of the resulting summed signal in the acoustic domain, the first and second waveforms are rectangular waves. The first waveform is delayed, in addition to any focusing delay, by a ¼ of a cycle relative to the second waveform. At the point in the body, the first and second waveform sum together to form a third waveform. The third waveform has three amplitude levels (0,1,2). The greatest amplitude is associated with an overlap of the first and second transmit waveforms and is preferably at the center of the third waveform. The number of cycles and amplitude shape of the first and second waveforms may also be controlled to create the desired third waveform in the acoustic domain.

Any of the various alternatives discussed above, such as pulse width modulation, filtering, generation of waveforms with multiple amplitudes and summation of waveforms in the acoustic domain may be used in combination. The combination may include more than two of the alternatives discussed above.

It should be understood that many changes and modifications can be made to the embodiments described above. For example, different ultrasound systems with different levels of programmability may be used. Different transducers and system configurations may also be used. Many of the various processes discussed above may be analog or digital processes. It is therefore intended that the foregoing detailed description be understood as an illustration of the presently preferred embodiments of the invention, and not as a definition of the invention. It is only the following claims, including all equivalents, that are intended to define the scope of the invention.

We claim:

1. In a method comprising the steps of (a) transmitting ultrasonic energy at a fundamental frequency and (b) receiving reflected ultrasonic energy at a harmonic of the fundamental frequency in an ultrasound system, the reflected ultrasonic energy responsive to the transmitted ultrasonic energy, an improvement wherein step (a) comprises the step of:

(a1) transmitting a uni-polar waveform comprising an amplitude shape rising gradually to a respective maximum value and falling gradually from said respective maximum value.

2. In a method comprising the steps of (a) transmitting ultrasonic energy at a fundamental frequency and (b) receiving reflected ultrasonic energy at a harmonic of the fundamental frequency in an ultrasound system, the reflected ultrasonic energy responsive to the transmitted ultrasonic energy, an improvement wherein step (a) comprises the step of:

(a1) transmitting a waveform characterized by an amplitude change rate of 8 or fewer times a carrier cycle, said waveform comprising an amplitude shape rising gradually to a respective maximum value and falling gradually from said respective maximum value.

3. The method of claim 1 or 2 wherein the step (a1) comprises transmitting a waveform characterized by said amplitude change rate of 4 times per said carrier cycle.

4. The method of claim 1 or 2 wherein the step (a1) comprises (a2) generating said waveform characterized by a carrier signal and an envelope signal.

5. The method of claim 4 wherein the step (a1) further comprises (a3) generating said waveform characterized by the envelope signal sampled at a rate corresponding to a multiple of a center frequency of the carrier signal.

6. The method of claim 5 wherein the step (a3) comprises generating said waveform characterized by the envelope signal sampled at 4 times the carrier center frequency.

7. The method of claim 4 wherein the step (a1) further comprises (a3) generating said waveform characterized by the carrier signal sampled at a rate corresponding to a multiple of a carrier center frequency.

8. The method of claim 7 wherein the step (a3) comprises generating said waveform characterized by the carrier signal sampled at a rate corresponding to two times the carrier center frequency.

9. The method of claim 4 wherein the step (a1) further comprises (a3) generating said waveform characterized by setting a phase of the envelope signal relative to a phase of the carrier signal.

10. The method of claim 4 wherein the step (a2) comprises generating said waveform characterized by amplitude modulating said carrier signal with said envelope signal.

11. The method of claim 10 wherein the step (a2) comprises modulating said envelope signal and said carrier signal with a multiplier.

12. The method of claim 4 wherein the step (a2) comprises generating said waveform characterized by setting the width of the envelope signal.

13. The method of claim 4 wherein the step (a2) comprises generating said waveform characterized by setting the amplitude levels of the envelope signal.

14. The method of claim 13 wherein the step (a2) comprises generating said waveform as a function of a number of amplitude levels selected from the group of 4, 8, and 16.

15. The method of claim 13 wherein the step (a2) further comprises setting said amplitude levels associated with said waveform digitally.

16. The method of claim 15 wherein the step (a2) comprises setting said amplitude levels corresponding to multiple bit words selected from the group of: thermometer code, binary code, gray-code, specific weighted code and a combination thereof.

17. The method of claim 4 wherein the step (a1) further comprises generating said waveform characterized by said envelope signal comprising a time sequence of amplitudes with a symmetrical distribution of amplitude levels about the peak as a function of time.

18. The method of claim 1 or 2 wherein the step (a1) comprises (a2) generating said waveform comprising a uni-polar waveform and characterized by an offset waveform summed with a bi-polar waveform.

19. The method of claim 18 wherein the step (a2) comprises generating said waveform characterized by said offset waveform comprising a property selected from the group of: gradually increasing and decreasing shape, duration, and a combination thereof.

20. The method of claim 19 wherein the step (a2) comprises generating said waveform characterized by said offset waveform comprising said gradually increasing and decreasing shape and said duration, said duration comprising a plurality of cycles of said bi-polar waveform.

21. The method of claim 20 wherein the step (a2) comprises generating said waveform characterized by said shape comprising stair stepped amplitude levels associated with sampling at a multiple of the carrier center frequency.

22. The method of claim 18 wherein the step (a2) comprises summing said offset waveform and said bi-polar waveform with a summer in real time transmission.

23. The method of claim 4 or 18 wherein the step (a1) comprises generating said waveform in response to control signals responsive to said characterizations.

24. The method of claim 1 or 2 wherein the step (a1) comprises (a2) transmitting said waveform comprising at least one pulse.

25. The method of claim 24 wherein the step (a2) comprises summing a first rectangular waveform with a second rectangular waveform, wherein said second rectangular waveform is 90 degrees out of phase with said first rectangular waveform.

26. The method of claim 1 or 2 wherein the step (a1) comprises transmitting said waveform comprising a shaped waveform, said shaped waveform selected from the group of: shaped pulse, pulse to pulse amplitude shape and combinations thereof.

27. The method of claim 2 wherein said waveform comprises a bi-polar signal.

28. The method of claim 2 wherein said waveform comprises a uni-polar signal.

29. The method of claim 1 or 2 wherein said waveform comprises a rectangular waveform.

30. The method of claim 1 wherein said waveform comprises a first waveform and wherein the step (a1) further comprises:

setting a characteristic selected from the group of: a cycle delay in addition to a focus delay, an amplitude level in addition to apodization scaling, a number of cycles and a combination thereof of at least a first waveform applied to at least a first of a plurality of transducer elements relative to at least a second waveform applied to at least a second of said plurality of transducer elements as a function of a shape comprising a sum of said first and second waveforms; and transmitting ultrasonic energy responsive to at least said first and second waveforms from at least said first and second transducer elements, respectively, said ultrasonic energy summed at said point comprising said shape, wherein said shape rises gradually to a respective maximum value and falls gradually from said respective maximum value.

31. The method of claim 1 wherein the step (a1) further comprises the step of modulating a pulse width of pulses within said waveform.

32. The method of claim 1 further comprising the step or steps of any combination of two or three of steps a3 and a4:

(a3) wherein said waveform comprises a first waveform, further comprising the steps of:
  (i) setting a characteristic selected from the group of: a cycle delay in addition to a focus delay, an amplitude level in addition to apodization scaling, a number of cycles and a combination thereof of at least a first waveform applied to at least a first of a plurality of transducer elements relative to at least a second waveform applied to at least a second of said plurality of transducer elements as a function of a shape comprising a sum of said first and second waveforms; and
  (ii) transmitting ultrasonic energy responsive to at least said first and second waveforms from at least said first and second transducer elements, respectively, said ultrasonic energy summed at said point comprising said shape, wherein said shape rises gradually to a respective maximum value and falls gradually from said respective maximum value; and (a4) modulating the pulse width of pulses within at least said first waveform.

33. An ultrasound apparatus for transmitting ultrasonic energy at a fundamental frequency for receipt of reflected ultrasonic energy at a harmonic of the fundamental frequency, the reflected ultrasonic energy responsive to the transmitted ultrasonic energy, comprising:

a transducer; and a signal generator for transmitting a uni-polar waveform comprising an amplitude shape rising gradually to a respective maximum value and falling gradually from said respective maximum value.

34. An ultrasound apparatus for transmitting ultrasonic energy at a fundamental frequency for receipt of reflected ultrasonic energy at a harmonic of the fundamental frequency, the reflected ultrasonic energy responsive to the transmitted ultrasonic energy, comprising:

a transducer; and a signal generator for transmitting a waveform comprising 8 or fewer samples per carrier cycle and an amplitude shape rising gradually to a respective maximum value and falling gradually from said respective maximum value.

35. The apparatus of claim 33 or 34 further comprising a summer, wherein said waveform comprises an off-set waveform summed with a bi-polar waveform.

36. The apparatus of claim 33 or 34 further comprising a multiplier, wherein said waveform comprises an envelope signal multiplied with a carrier signal.

37. The apparatus of claim 33 or 34 wherein said signal generator comprises a waveform generator for generating said waveform in response to stored data representing said waveform.

38. In a method comprising the steps of (a) transmitting ultrasonic energy at a fundamental frequency and (b) receiving reflected ultrasonic energy at a harmonic of the fundamental frequency in an ultrasound system, the reflected ultrasonic energy responsive to the transmitted ultrasonic energy, an improvement wherein step (a) comprises the step of:

(a1) generating a stepped pulse comprising an amplitude shape rising gradually to a respective maximum value and falling gradually from said respective maximum value.

39. The method of claim 38 wherein the step (a1) further comprises generating a second stepped pulse, wherein said first and second pulse comprise a bi-polar waveform.

40. The method of claim 38 wherein the step (a) comprises transmitting said stepped pulse.

41. The method of claim 38 wherein the step (a) further comprises filtering said stepped pulse waveform.

42. The method of claim 38 wherein the step (a) further comprises generating a plurality of said stepped pulses as a waveform.

43. The method of claim 42 wherein the step (a) further comprises generating said waveform characterized by a maximum value of one of said plurality of stepped pulses different from a maximum value of another of said stepped pulses.

44. The method of claim 38 wherein the step (a1) comprises summing a first rectangular pulse with a second rectangular pulse to form said stepped pulse, wherein said second rectangular waveform is 90 degrees out of phase with said first rectangular waveform.

45. In a method comprising the steps of (a) transmitting ultrasonic energy at a fundamental frequency and (b) receiving reflected ultrasonic energy at a harmonic of the fundamental frequency in an ultrasound system, the reflected ultrasonic energy responsive to the transmitted ultrasonic energy, an improvement wherein step (a) comprises the step of:

(a1) generating a waveform comprising a plurality of amplitudes selected from the group of: a plurality of positive amplitudes and a plurality of negative amplitudes, wherein said amplitudes each comprise a duration representing a step and corresponding to a sample rate less than or equal to 8 times the fundamental frequency, wherein an amplitude shape associated with said amplitudes rises gradually to a respective maximum value and falls gradually from said respective maximum value.

46. The method of claim 45 wherein the step (a1) comprises generating a uni-polar waveform.

47. The method of claim 45 wherein the step (a1) comprises generating a bi-polar waveform.

48. The method of claim 45 wherein the step (a1) comprises (a2) repeating the step (a1).

49. The method of claim 48 wherein the step (a2) comprises generating a series of shaped pulses.

50. A method of generating a waveform transmitted from at least one of a plurality of transducer elements for harmonic imaging responsive to transmission of the waveform in an ultrasound system comprising the steps of:

(a1) generating a waveform carrier signal associated with a fundamental frequency;

(a2) modulating said rectangular wave carrier signal with an envelope signal comprising a gradually increasing and gradually decreasing amplitude; and (a3) transmitting a waveform responsive to data created in step (a2) and sampled at 8 samples or less for each cycle of said carrier signal.

51. A method of generating a uni-polar waveform transmitted from at least one of a plurality of transducer elements for harmonic imaging in an ultrasound system comprising the steps of:

(a1) generating a bi-polar waveform;

(a2) off-setting said bi-polar waveform with an off-set signal comprising a gradually increasing and gradually decreasing amplitude; and (a3) transmitting said uni-polar waveform responsive to data created in step (a2).

* * * * *

UNITED STATES PATENT AND TRADEMARK OFFICE
CERTIFICATE OF CORRECTION

PATENT NO. : 5,913,823
DATED : June 22, 1999
INVENTOR(S) : David J. Hedberg et al.

It is certified that error appears in the above-indentified patent and that said Letters Patent is hereby corrected as shown below:

In column 9, line 17, change "SA" to --5A--.

In column 9, line 54, change "SA" to --5A--.

Signed and Sealed this

Eighteenth Day of April, 2000

*Attest:*

Q. TODD DICKINSON

*Attesting Officer*      *Director of Patents and Trademarks*